(12) United States Patent
Niederberger et al.

(10) Patent No.: US 9,504,782 B2
(45) Date of Patent: *Nov. 29, 2016

(54) PACKAGE FOR HYDROPHILIC MEDICAL INSTRUMENTS

(71) Applicant: Roche Diabetes Care, Inc., Indianapolis, IN (US)

(72) Inventors: Brigitte Niederberger, Thalwil (CN); Volker Zimmer, Morbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/043,364

(22) Filed: Oct. 1, 2013

(65) Prior Publication Data

US 2014/0027328 A1    Jan. 30, 2014

Related U.S. Application Data

(63) Continuation of application No. 12/396,932, filed on Mar. 3, 2009, now Pat. No. 8,567,602, which is a continuation of application No. PCT/EP2007/059195, filed on Sep. 3, 2007.

(30) Foreign Application Priority Data

Sep. 4, 2006  (EP) .................................... 06120033

(51) Int. Cl.
*B65D 83/10* (2006.01)
*A61M 5/00* (2006.01)
(Continued)

(52) U.S. Cl.
CPC ............ *A61M 5/002* (2013.01); *A61B 5/1411* (2013.01); *A61B 5/150022* (2013.01); *A61B 5/150305* (2013.01); *A61B 50/3001* (2016.02); *B65B 55/12* (2013.01)

(58) Field of Classification Search
CPC ............ A61M 5/002; A61M 5/3202; A61M 5/3216; A61M 5/03205; A61B 50/3001; A61B 5/1411; A61B 5/150305; A61B 5/150022; B65B 55/12
USPC ........ 206/438, 439, 63.3, 484, 484.1, 484.2, 206/384

See application file for complete search history.

(56) References Cited

U.S. PATENT DOCUMENTS

| 3,442,686 A | 5/1969 | Jones |
| 4,442,836 A | 4/1984 | Meinecke et al. |

(Continued)

FOREIGN PATENT DOCUMENTS

| DE | 28 03 345 B1 | 6/1979 |
| EP | 1 360 935 A1 | 11/2003 |

(Continued)

OTHER PUBLICATIONS

Canadian Patent Application No. 2,662,470 Office Action mailed Nov. 17, 2011.

(Continued)

*Primary Examiner* — Chun Cheung
(74) *Attorney, Agent, or Firm* — Woodard Emhardt Moriarty McNett and Henry LLP

(57) ABSTRACT

A plastic package for hydrophilic articles, in particular for hydrophilically coated medical instruments, is intended to ensure the hydrophilic nature of the enclosed instrument over a long period of time. The package includes at least one receiving compartment with a medical instrument for insertion into body tissue and is characterized in that, after sterilization by radiation, it has a proportion of volatile constituents of ≤0.1 µg/cm2.

24 Claims, 4 Drawing Sheets

(51) Int. Cl.
*A61B 5/15* (2006.01)
*B65B 55/12* (2006.01)

(56) References Cited

U.S. PATENT DOCUMENTS

| | | | |
|---|---|---|---|
| 4,813,210 A * | 3/1989 | Masuda | A61L 2/26 206/210 |
| 5,421,981 A | 6/1995 | Leader et al. | |
| 5,554,166 A | 9/1996 | Lange et al. | |
| 6,908,453 B2 | 6/2005 | Fleming et al. | |
| 2001/0054562 A1* | 12/2001 | Pettersson et al. | 206/364 |
| 2003/0211619 A1 | 11/2003 | Olson et al. | |
| 2004/0074794 A1* | 4/2004 | Conway | A61M 25/002 206/364 |
| 2004/0133172 A1 | 7/2004 | Wilkinson | |
| 2006/0030788 A1 | 2/2006 | Wong et al. | |
| 2006/0100404 A1* | 5/2006 | Gust et al. | 526/230.5 |
| 2006/0247555 A1 | 11/2006 | Harttig | |
| 2006/0263404 A1 | 11/2006 | Nielsen et al. | |

FOREIGN PATENT DOCUMENTS

| | | |
|---|---|---|
| EP | 1 887 355 | 2/2008 |
| WO | WO 98/48695 A1 | 11/1998 |
| WO | WO 00/30696 A1 | 6/2000 |
| WO | WO 2004/075760 A1 | 9/2004 |
| WO | WO 2004/075944 A2 | 9/2004 |
| WO | WO 2005/104948 A1 | 11/2005 |

OTHER PUBLICATIONS

DE 28 03 345 B1 filed Jun. 13, 1979—English Language Translation.
European Application No. 06 120 033.3 Office Action mailed Mar. 19, 2010.
International Application PCT/EP2007/059195 International Preliminary Report on Patentability/Written Opinion mailed Mar. 19, 2009.
International Application PCT/EP2007/059195 International Preliminary Report on Patentability/Written Opinion Translation mailed Mar. 26, 2009.
International Application PCT/EP2007/059195 International Search Report mailed Jan. 21, 2008.
Römpp, Chemie Lexikon, Thieme Verlag Stuttgart, 10th extended edition, 1996, vol. P1-S, pp. 3527 to 3528.

* cited by examiner

PACKAGE FOR HYDROPHILIC MEDICAL INSTRUMENTS

CROSS REFERENCE TO RELATED APPLICATION

This application is a continuation of U.S. patent application Ser. No. 12/396,932 filed Mar. 3, 2009, which is a continuation of International Application No. PCT/EP2007/059195, filed Sep. 3, 2007, which claims the benefit of European Patent Application No. EP 06 120 033.3, filed Sep. 4, 2006, the entire disclosures of which are hereby incorporated by reference.

BACKGROUND

The invention relates to a plastic package for hydrophilic medical instruments, in particular for hydrophilically coated lancets, which package ensures the hydrophilic nature of the enclosed article over a long period of time.

In medical diagnostics, examination of blood samples or of interstitial fluids permits early and reliable detection of pathological conditions and also specific and reliable monitoring of physical states. Medical diagnostics always entails obtaining a sample of blood or of interstitial fluid from the individual who is to be examined.

To obtain this sample, the skin of the person to be examined can be punctured, for example at the finger pad or ear lobe, with the aid of a sterile, sharp lancet, in order in this way to obtain a few microliters of blood for the analysis. This sampling method is particularly suitable for sample analysis that is carried out directly after the sample has been obtained.

In the area of home monitoring in particular, in other words where persons without specialist medical training carry out simple analyses of blood or of interstitial fluid themselves, and particularly for diabetics taking blood samples on a regular basis, several times a day, to monitor their blood glucose concentration, lancets and associated devices (puncturing aids) are available. These puncturing aids allow samples to be taken with the least possible discomfort and in a reproducible manner, in particular by persons who have no specialist medical training Lancets and devices of this kind are the subject matter of, for example, WO-A 98/48695, U.S. Pat. Nos. 4,442,836 or 5,554,166.

Self-monitoring of blood glucose levels, often carried out at home, is a method of diabetes control that is nowadays applied worldwide. Blood glucose meters in the prior art comprise an analysis device into which a test element (test strip) is inserted. The test element is brought into contact with a droplet of a sample which has been obtained shortly before by means of a puncturing aid, for example from the pad of a finger.

The numerous system components (lancet, puncturing aid, test element and analysis device) require a lot of space and involve quite complex handling. However, systems have in the meantime been developed which have a greater degree of integration and are thus easier to handle and in which, for example, the test elements are stored in the analysis device and made available for measurement. The next step in terms of miniaturization is, for example, the integration of several functions or function elements within a single analytical aid (disposable). The operating sequence can be greatly simplified by suitable combination of the puncturing procedure and of the sensor-based analysis on a test element.

In the prior art, for example, it is known to provide the lancets of such analytical aids with a capillary structure or to make them part of a capillary structure (in this connection see WO 2005/104948 A1). In this case, after the skin has been punctured and the sample emerges, the lancet tip is brought into contact with the sample in order to collect said sample with the aid of the capillary.

The lancet tip for collecting blood or interstitial fluids is typically sterilized in advance and kept in a sterile state by a sterile protector (for example in the form of a cap or pocket) before being used for a puncturing procedure. This ensures that the lancet tip is not contaminated by its surroundings. Moreover, measures are also taken to ensure that, after the skin has been punctured, the lancet tip is shielded (if appropriate by the same cap or pocket), such that accidental injuries and associated infections caused by fluids adhering to the lancet tip are avoided.

In the case of individual lancets, a sterile protector can be produced, for example, by means of the lancet tip being encapsulated with plastic by injection molding in a single operation with the formation of the lancet body. Before use, the user removes this part manually, generally upon insertion of the lancet into the puncturing aid. In the case of lancets stored in a magazine, similar sterile protection devices are customary, for example devices in which the lancet is drawn rearward out of a sterile protector, whereupon the sterile protector is conveyed out of the puncturing path by a spring force. Relatively complicated mechanisms, in particular springs integrated into the equipment, are required for this.

Numerous packages for the medical aids described above have been described in the prior art.

EP 1 360 935 A1 describes a tape-like package for a large number of medical aids. The aids are accommodated in depressions in a first tape section that are covered by a second tape section. To ensure the sterile nature of the medical aids, they are sealed by welding in a flexible packaging material.

DE 28 03 345 B1 describes a blood sampling device with a needle that can be moved against the surface of a patient's body by the action of a force. The needles are stored in what are called strip packages, which comprise contiguous pockets. The strip packages are composed of a bottom film and a cover film of paper, plastic sheet or the like, the bottom film and cover film being placed on each other and connected to each other in a ladder-shaped pattern so as to form pockets that enclose the blood lancets on all sides.

WO 2004/075760 A1 relates to an automatically opening package for medical aids that comprises an upper flexible sheet section which has a distal end, a proximal end, a first peripheral edge and a second peripheral edge, and around it a flexible sheet section which has a distal end, a proximal end, a first peripheral edge and a second peripheral edge. The upper and lower flexible sheet sections are designed such that they can be detachably sealed together along at least one segment of their first and second peripheral edges, as a result of which a medical device is enclosed within the upper and lower flexible sheet sections. A collar is mounted on the distal end of the upper flexible sheet section and on the distal end of the lower flexible sheet section, said collar being mounted on the distal ends of the lower and upper flexible sheet sections in such a way that a relative sliding movement of the collar and of the proximal ends of the upper and lower flexible sheet sections that decreases a distance between them causes the upper and lower flexible sheet sections to pull apart. In this way, the package is automatically opened and at least one section of the medical device is exposed.

Moreover, WO 2005/104948 A1 discloses a test magazine with two film tapes which are connected to each other in a sandwich formation and can be wound up and between which there are receiving compartments for test elements, these each comprising a puncturing unit for puncturing body tissue and a test unit to which body fluid is applied.

Lancets and in particular microneedles with capillaries are customarily made of surgical steel, for example a stainless chromium-alloy heat-treated steel with a low carbon content (material number 1.4021), which can pose a problem as regards sampling of blood and interstitial fluids by means of capillary forces. The reason for this lies in the hydrophobic nature of the steel, which at least partially prevents filling of the capillary by means of capillary forces. In order nevertheless to achieve complete or almost complete filling of the capillary, the capillary is usually provided with a hydrophilic coating, in particular with a coating of $SiO_2$, $TiO_2$, polyacrylic acid or dextran sulfate. The hydrophilic surfaces are highly energetic, which has the effect that they gradually reduce their surface energy by absorption of gas molecules onto their surface, and this, in the case of absorption of apolar compounds, leads step by step to a loss of the hydrophilic nature of the coating. The above-described prior art provides no teaching aimed at ensuring the hydrophilic nature of the surfaces of lancets, puncturing aids and medical aids preferably over a long period of time.

SUMMARY

The object of the present invention is therefore to avoid the disadvantages of the prior art and, in particular, to make available a package for hydrophilic articles, such as hydrophilic medical instruments, microneedles with capillaries, lancets and medical aids, which package permanently ensures the hydrophilic nature of the article enclosed by the package.

According to the invention, this object is achieved by a plastic package comprising at least one receiving compartment with at least one partially hydrophilic medical instrument for insertion into body tissue, which package, after sterilization by radiation, has a proportion of volatile constituents of $\leq 0.1$ µg/cm$^2$, preferably of $\leq 0.01$ µg/cm$^2$. It has in fact been found that, by reducing the highly volatile components released from the packaging material to concentrations of $\leq 0.1$ µg/cm$^2$, it is possible to ensure permanent functionality of the medical instruments preferably provided with a hydrophilic layer. In the present case, "permanent" is to be understood as meaning that, at least after about three months of storage in the package according to the invention, the wetting properties of the hydrophilically coated medical instrument are identical to those prior to its storage.

According to the invention, the term "plastic package" is to be understood as meaning an envelope made of plastic which protects the enclosed medical instrument from external contamination and loss of sterility. It is thus intended to ensure as far as possible a permanent sterility of the instrument. According to the invention, the package is made from plastic and is thus composed 100% of plastic. In one embodiment of the invention, the package comprises a plastic or a mixture of plastics as packaging material in addition to further materials, for example metal films. In this case, the proportion of plastic can be varied within wide limits, for example in the range between 90% by weight to 10% by weight and 10% by weight to 90% by weight.

According to the invention, the term "medical instrument" is to be understood as meaning puncturing aids, lancets, microneedles, particularly preferably microneedles with a capillary, and medical aids with a similar action.

Medical instruments of these kinds are preferably used to collect samples of blood or interstitial fluids.

The term "volatile constituents" is to be understood as meaning constituents of the package that are gradually released by the latter. The word "volatile" implies here that the substances belonging to the group of highly volatile constituents evaporate on account of their high vapor pressure or low boiling point. The volatile constituents are, for example, plasticizers such as phthalates. The volatile constituents can be characterized and quantified by means of headspace gas chromatography, for example.

According to the invention, the plastic package is a package that encloses a medical instrument, preferably a lancet for puncturing body tissue. The medical instrument is chosen from the group comprising puncturing aids, lancets, microneedles, particularly preferably microneedles with a capillary, and medical aids.

To improve the uptake of blood or interstitial fluids, the medical instruments described above are at least partially hydrophilic and are provided preferably at least in some sections with a hydrophilic coating. The hydrophilic coating provided in some sections is applied particularly at those places that come into contact with blood or interstitial fluid during sampling. This advantageously ensures that coated capillaries made of surgical steel, for example, are also filled completely or almost completely with the test fluid.

In one embodiment of the invention, the package comprises polyester, in particular polyethylene terephthalate (PET), as packaging material in addition to further materials. The proportion of polyester can be varied within wide limits, for example in the range from 100:1 to 1:100. In another embodiment, the package is made mainly of polyester, i.e. one or more further materials can be present in addition to polyester, but only in very small quantities below 1% by weight. In another embodiment, the package can be made of polyester, i.e. composed 100% of polyester.

Polyester is the name for polymers of the general formulae I and II:

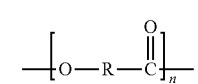

Formula I

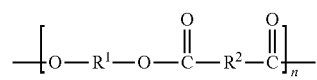

Formula II

In this connection see Römpp, Chemie Lexikon, Thieme Verlag Stuttgart, 10th extended edition, 1996, volume Pl-S, pages 3527 to 3528. This passage from the literature is incorporated by reference into the present application.

Polyesters are produced by ring-opening reactions of lactones (I) or by polycondensation of hydroxy-carboxylic acids (I) or diols and carboxylic acid (derivatives) (II). Branched and crosslinked polyesters are obtained in the polycondensation of trihydric or polyhydric alcohols with polyfunctional carboxylic acids. Polyesters are generally considered also to include polycarbonates (polyesters of carbonic acid).

Polyesters of type I are, among others, polyglycolic acids, polylactic acids, polyhydroxybutyric acid, poly(ε-caprolactone) and polyhydroxybenzoic acids.

Purely aliphatic polyesters of type II are polycondensates of aliphatic diols and dicarboxylic acids, which are used inter alia as products with terminal hydroxyl groups as polydiols for the production of polyester urethanes. Polyesters of type II from aliphatic diols and aromatic dicarboxylic acids are the most important in terms of quantity, in particular polyalkylene terephthalates with polyethylene terephthalate (PET), polybutylene terephthalate (PBT), poly (1,4-cyclohexanedimethylene terephthalate) as the most important representatives.

Purely aromatic polyesters are the polyarylates which include inter alia poly(4-hydroxybenzoic acid), polycondensates of bisphenol A and phosgene.

In addition to the aforementioned polyesters, unsaturated polyesters can also be produced from unsaturated dicarboxylic acids and are technically important as polyester resins, in particular as unsaturated polyester resins (UP resins). According to one embodiment of the invention, polyethylene terephthalate (PET) is preferred as polyester.

A person skilled in the art will choose the wall thickness of the plastic package as a function of the article that is to be packaged. According to one embodiment of the invention, the package has a wall thickness of 1 to 500 µm, preferably of 20 to 80 µm, particularly preferably of 30 µm. A wall thickness within the aforementioned range ensures that the package does not suffer damage during storage or transport and does not become permeable to contaminants, bacteria and dirt.

The wall of the plastic package according to the invention preferably has a single-layer structure.

According to another embodiment of the invention, the wall of the package is composed of several layers. In this case, the package is preferably characterized in that the innermost layer mainly comprises polyester or is made of polyester. The advantage of using polyester as the wall material of the package according to the invention is that this polymer material releases only a small proportion of highly volatile constituents, such as plasticizers, even at temperatures of approximately 60° C. In this way, the functionality of the instrument located in the package is ensured over a long period of time, since only relatively small amounts of the released components can settle on the hydrophobic coating of the instrument.

In a particularly preferred embodiment, the package also encloses a test unit to which body fluid is to be applied. According to another embodiment of the invention, the medical instrument, preferably the puncturing aid, and test unit are arranged separately from each other in separate receiving compartments. The compartments can be realized, for example, simply by the intermediate area between the unformed films. Their separation also affords advantages in terms of the fact that the puncturing aid can be independently pretreated, in particular sterilized and made hydrophilic, without damage to the test chemicals, and that there is no danger of test chemicals getting into the body during the puncturing procedure.

According to the invention, the medical instruments contained in the associated receiving compartments formed by the package are sterilized by radiation, preferably via a mask for screening the test units. Since hydrophilic coatings are extremely sensitive and, moreover, since glucose test strips, for example, are packaged together with the medical instrument, the sterilization methods that are particularly preferred are those involving sterilization by radiation. Consequently, the package, serving as a package for the medical instrument, is characterized by being sterilized by β or γ radiation, particularly preferably by β radiation.

According to the invention, suitable films for the packaging of hydrophilically coated medical instruments or of instruments coated with hydrophilic coatings are films with a thickness of preferably 30 µm which have a proportion of volatile constituents of ≤0.1 µg/cm$^2$, preferably of ≤0.01 µg/cm$^2$, after sterilization by β radiation. In particular, in comparative tests, polyester films (regardless of the manufacturer) showed very good results in the analysis of the volatile constituents by gas chromatography. Such films have hitherto mostly been used for the packaging of foodstuffs.

The following examples and comparative examples explain the invention but are not intended to define it or to limit it in any way.

DESCRIPTION OF THE SELECTED EMBODIMENTS

Figure 1:
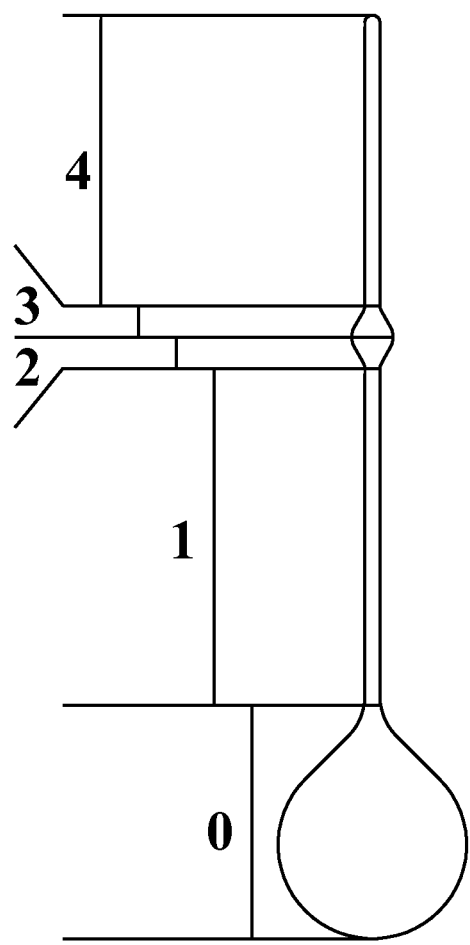
FIG. 1: Capillary and associated evaluation scheme for testing a package according to the invention.

FIG. 1 shows an example of a capillary. The illustrated scale from 0 to 4 indicates the filling behavior of the capillary. The value 1 on this scale denotes poor filling of the capillary, while the value 4 denotes very good filling. Capillaries characterized by the value 4 permit complete or almost complete filling of the capillary with blood or interstitial fluid.

To find out which films or materials are suitable for achieving the object according to the invention, a film screening was carried out. The proportions of volatile constituents of different films/pouches were determined by headspace gas chromatography. The corresponding results are set out in Table 1 and show that polyester films with few additives have the lowest proportions of volatile constituents after β sterilization.

TABLE 1

Proportion of volatile constituents of different films.
The values marked * indicate the thickness of the respective film as determined by a micrometer.

| | | | Proportion of volatile constituents [µg/cm$^2$] | |
| --- | --- | --- | --- | --- |
| Film/pouch | Manufacturer | Thickness [µm] | un-treated | After β-sterilization |
| Melinex S (polyester) | DuPont | 20* | <0.01 | 0.01 |
| Hostaphan RN 23 MED (polyester) | Mitsubishi | 23 | <0.01 | 0.01 |
| Hostaphan RN 19 (polyester) | Mitsubishi | 19 | <0.01 | 0.01 |
| Mylar 850 (polyester) | DuPont | 20 | <0.01 | 0.01 |

TABLE 1-continued

Proportion of volatile constituents of different films.
The values marked * indicate the thickness of the respective
film as determined by a micrometer.

| Film/pouch | Manufacturer | Thickness [μm] | Proportion of volatile constituents [μg/cm²] | |
|---|---|---|---|---|
| | | | untreated | After β-sterilization |
| Mylar 850 (polyester) | DuPont | 30 | 0.01 | 0.01 |
| Mitsubishi RHS 12 (polyester) | Mitsubishi | 12 | 0.01 | 0.01 |
| PA/PE | Medipack | 70* | 0.01 | 0.02 |
| Polialuvel polyester/ALU/PE | Medipack | 90* | 0.01 | 0.05 |
| Teflon | DuPont | 50* | 0.01 | 0.06 |
| Hostaphan RHS 30 (polyester) | Mitsubishi | 30 | 0.03 | 0.06 |
| Früh 24093 (PA/PE) | Früh | 90* | 0.03 | 0.06 |
| Alu/PE | Zewatener | 110* | 0.04 | 0.01 |
| Früh 24086 (PA/PE) | Früh | 90* | 0.16 | 0.16 |
| Topas 8007 F04 | Pütz Folien | 90 | 0.06 | 0.18 |
| Barex (acrylonitrile) | Früh | 50 | 0.11 | 0.31 |
| Topas 8007 PE Blend (COC/PE) | Pütz Folien | 70 | 0.28 | 0.41 |
| Sealed-edge pouch polyester O/ALU/PE, 12-9-75 | Sengewald Klinikprodukte | 96 | 0.4 | |

Figure 2:
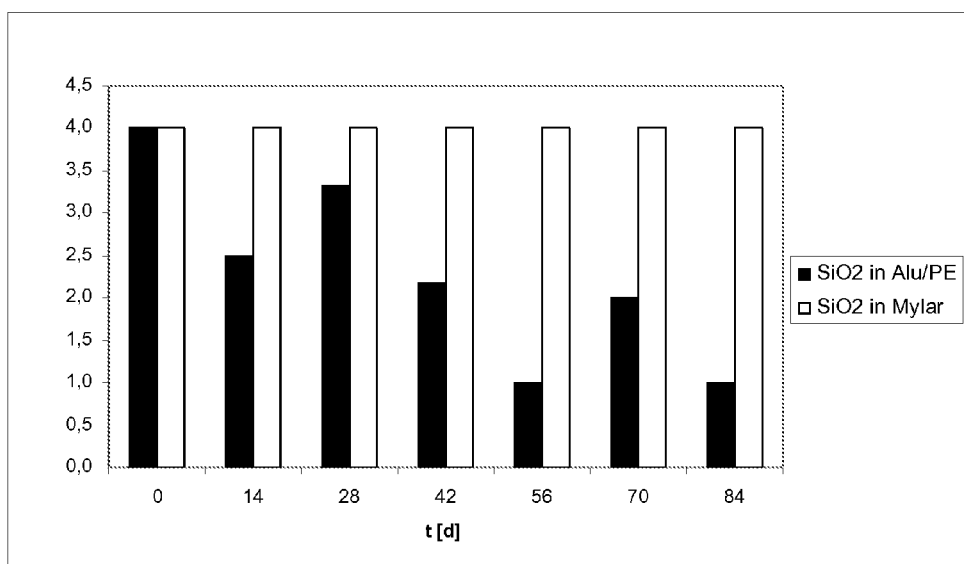
FIG. 2: Results of a storage test of test plates coated hydrophilically with SiO$_2$ in two different packages.

An experiment was then conducted to determine the storage stability of a hydrophilic coating in two different films. A total of 42 test plates, which had capillaries as shown in FIG. 1, were coated with a hydrophilic coating of $SiO_2$. Thereafter, 21 of the test plates were packaged in Alu/PE pouches from Zewatener and 21 were packaged in polyster-containing Mylar pouches from DuPont. The packaged test plates were then β-sterilized (25 kGy, 10 MeV) and stored for 12 weeks at 35° C. The plates were tested at 2-week intervals, with 1.5 μl of blood being pipetted into the reserve of the capillaries and the filling behavior of the respective capillary being evaluated on the basis of the evaluation scheme shown in FIG. 1. The results of the storage test are shown in FIG. 2. In this figure, the evaluation of the filling behavior of the capillaries (ranking from 1 to 4) is plotted against the storage time in days after the sterilization. As can be seen from FIG. 2, the capillaries of the test plates packaged in Mylar pouches (proportion of volatile constituents: 0.01 μg/cm²) show an optimal filling behavior over a period of 84 days, whereas the test plates packaged in Alu/PE pouches (proportion of volatile constituents: 0.06 μg/cm²) filled more poorly as the storage time increased. The results found by gas chromatography were therefore able to be confirmed experimentally.

The test for volatile components by gas chromatography was performed as follows:
Equipment, Accessories and Chemicals:
Gas Chromatograph: Carlo Erba HRGC 5300 with headspace, autosampler in split mode, or comparable equipment
Capillary: from Chrompack, order No. 7761, or comparable capillary
Type: Wcot fused silica
Stationary phase: CPSIL 8 CB
Film thickness: 1.12 um
i.d.: 0.32 mm
Length: 25 m
Glass Vessels and Kit:
Test vessels: 10 ml HS glass tube
Chemicals:
Toluene: Merck No. 1.09768.0005
Carbon disulfide: Merck p.a. No. 1.02214.1000 or chemicals of comparable quality
Partial Test for Volatile Constituents (GC)
Standard:
  20-25 mg of toluene were weighed accurately to 0.1 mg into a 50-ml flask. 50 ml of carbon disulfide were pipetted into this and weighed out. About 10 mg of this solution were weighed accurately to 0.1 mg into an HS glass tube and the latter was immediately closed.
  Two standard solutions were produced and each standard solution weighed into 3 HS glass tubes. The volatile constituents were calculated using the mean value of all the standards.
  The standard was temperature-controlled for at least one hour.
Sample Preparation/Quantity:
  A section of film measuring 50 cm² of the sample to be tested was cut into small pieces and placed in an HS glas tube. At least one sample was prepared per batch.
  Sample left to stand for 18 hours in the HS bath before analysis
Chromatography Conditions:
Temperature program:
$T_{start}$: 40° C., 5 min
Heating rate: 10° C./min
$T_{end}$: 280° C., 5 min
Partial Test Protocol for Volatile Constituents (GC)
Temperature of heating zones:
Mega 5300
Injector: 250° C.
Detector: 280° C.
HS bath: 100° C.
HS syringe: 100C
Gas supply:
Carrier gas: helium
Preliminary pressure: 0.5 bar
Split: 1:40
Detector: device-specific settings
FID
Att.: 7
Mult. factor: 1
Computer System: Chrom Card or comparable evaluation system
Injection Volume: 1.25 ml
Evaluation:
  The evaluation was performed by the external standard method. In this, the total surface area of all the volatile constituents is used for the calculation and the quantity is calculated with the aid of the toluene concentration and the toluene peak surface. The mean value is formed from all the results.

Figure 3:
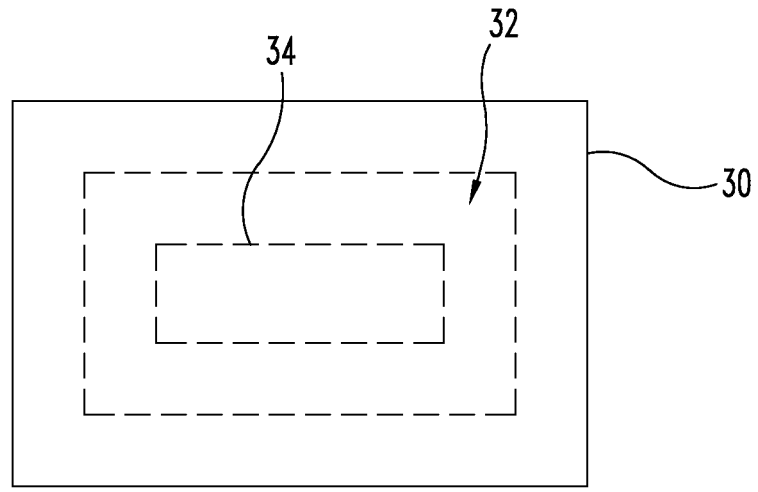
FIG. 3: Top view of a plastic package according to one embodiment.

FIG. 3 illustrates a plastic package 30 comprising at least one receiving compartment 32 with at least one partially hydrophilic medical instrument 34 for insertion into body tissue, which package, after sterilization by radiation, has a proportion of volatile constituents of ≤0.1 μg/cm², preferably of ≤0.01 μg/cm². It has in fact been found that, by reducing the highly volatile components released from the packaging material to concentrations of ≤0.1 μg/cm², it is possible to ensure permanent functionality of the medical instruments preferably provided with a hydrophilic layer.

Figure 4:
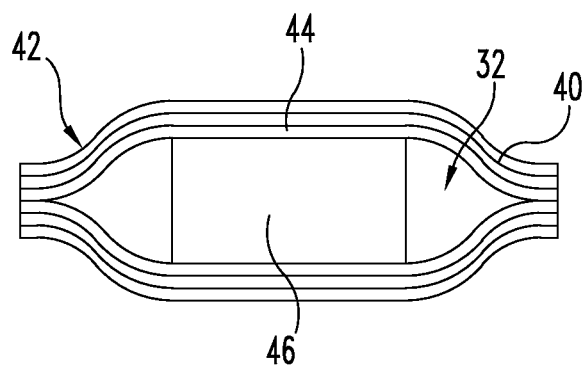
FIG. 4: Cross-sectional view of a plastic package according to another embodiment.

According to another embodiment illustrated in FIG. 4, the wall of a package 40 is composed of several layers 42.

In this case, the package 40 is preferably characterized in that an innermost layer mainly comprises polyester or is made of polyester. The advantage of using polyester as the wall material of the package according to the invention is that this polymer material releases only a small proportion of highly volatile constituents, such as plasticizers, even at temperatures of approximately 60° C. In this way, the functionality of the instrument located in the package is ensured over a long period of time, since only relatively small amounts of the released components can settle on the hydrophobic coating of the instrument.

In a particularly preferred embodiment, package 40 also encloses a test unit to which body fluid is to be applied. According to another embodiment of the invention, the medical instrument, preferably the puncturing aid, and test unit are arranged separately from each other in separate receiving compartments. The compartments can be realized, for example, simply by the intermediate area between the unformed films. Their separation also affords advantages in terms of the fact that the puncturing aid can be independently pretreated, in particular sterilized and made hydrophilic, without damage to the test chemicals, and that there is no danger of test chemicals getting into the body during the puncturing procedure.

Figure 5:
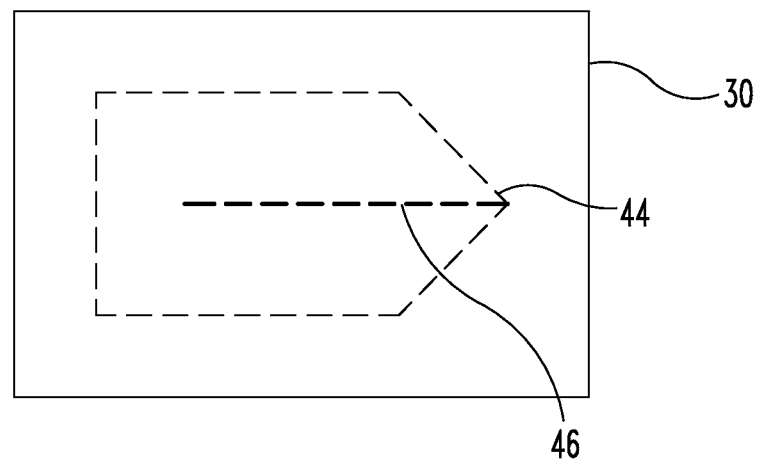
FIG. 5: A diagrammatic view of a package containing a microsampler according to another embodiment.

According to the invention, the plastic package 20 is a package that encloses a medical instrument, preferably a lancet for puncturing body tissue. In one example depicted in FIG. 5, the package 30 encloses a microneedle 44 with a capillary 46. To improve the uptake of blood or interstitial fluids, the medical instruments described above are at least partially hydrophilic and are provided preferably at least in some sections with a hydrophilic coating. The hydrophilic coating provided in some sections is applied particularly at those places that come into contact with blood or interstitial fluid during sampling. This advantageously ensures that coated capillaries made of surgical steel, for example, are also filled completely or almost completely with the test fluid.

Figure 6:
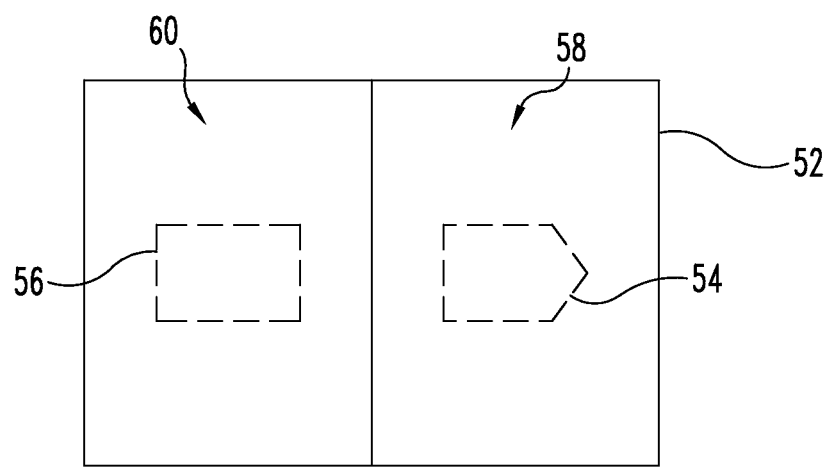
FIG. 6: A diagrammatic view of a package according to a further embodiment.

A package 52 according to another embodiment is illustrated in FIG. 6. As shown, a puncturing aid 54 and test unit 56 are arranged separately from each other in separate receiving compartments 58 and 60. The compartments 58 and 60 can be realized, for example, simply by the intermediate area between the unformed films. Their separation also affords advantages in terms of the fact that the puncturing aid 54 can be independently pretreated, in particular sterilized and made hydrophilic, without damage to the test chemicals, and that there is no danger of test chemicals getting into the body during the puncturing procedure.

The invention claimed is:

1. A packaging system, comprising:
a plastic package comprising at least one receiving compartment with at least one partially hydrophilic medical instrument for insertion into body tissue, characterized in that, after sterilization by radiation, the plastic package has a proportion of volatile constituents of ≤0.1 µg/cm².

2. The packaging system as claimed in claim 1, characterized in that the medical instrument is chosen from the group consisting of puncturing aids, lancets, medical aids and microneedles.

3. The packaging system as claimed in claim 1, characterized in that the medical instrument comprises a hydrophilic coating at least in some sections.

4. The packaging system as claimed in claim 1, characterized in that the plastic package is made of polyester.

5. The packaging system as claimed in claim 1, characterized in that the package has a wall thickness in the range of 1 to 500 µm.

6. The packaging system as claimed in claim 1, characterized in that the plastic package has a multi-layer structure.

7. The packaging system as claimed in claim 6, characterized in that the innermost layer is a layer of polyester.

8. The packaging system as claimed in claim 1, characterized in that the package encloses a test unit to which body fluid is to be applied.

9. The packaging system as claimed in claim 1, characterized in that the package is sterilized by β radiation.

10. The packaging system as claimed in claim 1, wherein the volatile constituents are constituents of the package that are successively released by the latter and the volatile constituents being characterized and quantified by means of headspace chromatography.

11. The packaging system as claimed in claim 10, wherein:
the medical instrument is chosen from the group consisting of puncturing aids, lancets, medical aids and microneedles; and
the medical instrument comprises a hydrophilic coating at least in some sections.

12. The packaging system as claimed in claim 1, wherein the medical instrument is a microneedle with a capillary coated with a hydrophilic coating.

13. A method, comprising:
placing at least one partially hydrophilic medical instrument into a compartment of a plastic package;
sterilizing by radiation the medical instrument in the plastic package; and
wherein the plastic package has a proportion of volatile constituents of ≤0.1 µg/cm² after said sterilizing by radiation.

14. The method of claim 13, wherein the medical instrument is a microneedle with a capillary coated with a hydrophilic coating.

15. The method of claim 13, wherein the medical instrument includes a hydrophilic coating at least in some sections.

16. The method of claim 13, wherein said sterilizing includes sterilizing by β radiation.

17. The method of claim 13, further comprising:
selecting material to produce the plastic package by selecting a material that has a proportion of volatile constituents of ≤0.1 µg/cm² after said sterilizing; and
producing the plastic package with the material.

18. The method of claim 17, wherein the material includes polyester.

19. A method, comprising:
applying a hydrophilic coating to at least one partially hydrophilic medical instrument;
placing the medical instrument into a compartment of a plastic package;
sealing the plastic package after said placing;
sterilizing by radiation the medical instrument in the plastic package; and
wherein the plastic package has a proportion of volatile constituents of ≤0.1 µg/cm² after said sterilizing by radiation.

20. The method of claim 13, further comprising:
quantifying the volatile constituents through headspace chromatography.

21. A packaging system, comprising:

a plastic package comprising at least one receiving compartment with at least one partially hydrophilic medical instrument for insertion into body tissue;

wherein the plastic package has a proportion of volatile constituents of ≤0.1 µg/cm² after sterilization by radiation; and wherein the medical instrument is chosen from the group consisting of puncturing aids, lancets, medical aids and microneedles.

22. A packaging system, comprising:

a plastic package comprising at least one receiving compartment with at least one partially hydrophilic medical instrument for insertion into body tissue;

wherein the plastic package has a proportion of volatile constituents of ≤0.1 µg/cm² after sterilization by radiation; and wherein the volatile constituents are constituents of the package that are successively released by the latter and the volatile constituents being characterized and quantified by means of headspace chromatography.

23. A method, comprising:

placing at least one partially hydrophilic medical instrument into a compartment of a plastic package, wherein the medical instrument is chosen from the group consisting of puncturing aids, lancets, medical aids and microneedles;

sterilizing by radiation the medical instrument in the plastic package; and wherein the plastic package has a proportion of volatile constituents of ≤0.1 µg/cm² after said sterilizing by radiation.

24. A method, comprising:

placing at least one partially hydrophilic medical instrument into a compartment of a plastic package;

sterilizing by radiation the medical instrument in the plastic package;

wherein the plastic package has a proportion of volatile constituents of ≤0.1 µg/cm² after said sterilizing by radiation; and wherein the volatile constituents are constituents of the package that are successively released by the latter and the volatile constituents being characterized and quantified by means of headspace chromatography.

* * * * *